US009277892B2

(12) United States Patent
Sanders (10) Patent No.: US 9,277,892 B2
(45) Date of Patent: Mar. 8, 2016

(54) DEVICE FOR MONITORING SLEEPING INDIVIDUALS

(71) Applicant: XEROX CORPORATION, Norwalk, CT (US)

(72) Inventor: Aaron D. Sanders, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 1 day.

(21) Appl. No.: 13/944,090

(22) Filed: Jul. 17, 2013

(65) Prior Publication Data

US 2015/0022343 A1    Jan. 22, 2015

(51) Int. Cl.
*G08B 19/00*    (2006.01)
*A61B 5/00*    (2006.01)
*G06F 19/00*    (2011.01)
*G08B 21/12*    (2006.01)
*A61B 5/11*    (2006.01)

(52) U.S. Cl.
CPC ............... *A61B 5/746* (2013.01); *A61B 5/1128* (2013.01); *A61B 5/4806* (2013.01); *G06F 19/3406* (2013.01); *A61B 5/1116* (2013.01); *A61B 5/747* (2013.01); *A61B 2503/04* (2013.01); *A61B 2560/0242* (2013.01); *G06F 19/3418* (2013.01); *G08B 21/12* (2013.01)

(58) Field of Classification Search
USPC ........................................................ 340/521
See application file for complete search history.

(56) References Cited

U.S. PATENT DOCUMENTS

| 4,862,144 | A | 8/1989 | Tao |
| 5,389,967 | A | 2/1995 | Kim |
| 5,505,199 | A | 4/1996 | Kim |
| 5,515,865 | A | 5/1996 | Scanlon |
| 5,704,367 | A | 1/1998 | Ishikawa et al. |
| 6,011,477 | A * | 1/2000 | Teodorescu et al. ........ 340/573.1 |
| 6,032,004 | A | 2/2000 | Mirabella, Jr. et al. |
| 6,208,897 | B1 | 3/2001 | Jorgenson et al. |
| 6,373,392 | B1 | 4/2002 | Au |
| 6,492,634 | B2 | 12/2002 | Marchitto et al. |
| 7,035,432 | B2 | 4/2006 | Szuba |

(Continued)

FOREIGN PATENT DOCUMENTS

| WO | 8700415 | 1/1987 |
| WO | 9112051 | 8/1991 |

(Continued)

*Primary Examiner* — Ojiako Nwugo (74) *Attorney, Agent, or Firm* — Gibb & Riley, LLC (57) ABSTRACT

Methods and apparatuses monitor and evaluate the movement and sounds of an individual in a sleeping structure to identify individual movement and sound activities that are outside acceptable movement and sound tolerances. Similarly, the methods and apparatuses monitor and evaluate the gases surrounding the individual and the temperature and humidity to identify environmental conditions that are outside acceptable environmental tolerances. The methods and apparatuses constantly and dynamically change the acceptable movement and sound tolerances and the acceptable environmental tolerances based on the age of the individual and based on historical monitoring of the movement and sounds of the individual, historical monitoring of the gases surrounding the individual, and historical monitoring of the temperature and humidity surrounding the individual. The methods and apparatuses cause the input/output device to provide an audible warning and at least one electronic message warning based on movement, sound, and environmental conditions being outside acceptable tolerances.

24 Claims, 4 Drawing Sheets

(56) References Cited

U.S. PATENT DOCUMENTS

| | | |
|---|---|---|
| 7,961,093 B2 | 6/2011 | Chiao et al. |
| 8,257,268 B2 | 9/2012 | MacLeod et al. |
| 2002/0133067 A1 | 9/2002 | Jackson, III |
| 2005/0143617 A1* | 6/2005 | Auphan .......................... 600/26 |
| 2006/0097879 A1 | 5/2006 | Lippincott |
| 2010/0076333 A9 | 3/2010 | Burton et al. |
| 2011/0019059 A1 | 1/2011 | Mizutani et al. |
| 2012/0083670 A1 | 4/2012 | Rotondo et al. |
| 2012/0319835 A1 | 12/2012 | Schulmeister et al. |
| 2013/0043999 A1* | 2/2013 | Van Beest ................... 340/573.7 |
| 2013/0165809 A1* | 6/2013 | Abir ............................... 600/534 |
| 2015/0051451 A1* | 2/2015 | Kido ............................. 600/301 |

FOREIGN PATENT DOCUMENTS

| | | |
|---|---|---|
| WO | 9740748 | 11/1997 |
| WO | 0072748 | 12/2000 |
| WO | 2004049109 | 6/2004 |
| WO | 2005010535 | 2/2005 |
| WO | 2006008745 | 1/2006 |

* cited by examiner

DEVICE FOR MONITORING SLEEPING INDIVIDUALS

BACKGROUND

Systems and methods herein generally relate to monitoring devices and methods and more particularly to devices and methods that monitor individuals while they sleep.

Many medical problems surface while individuals are sleeping, and devices that monitor sleeping individuals are useful for detecting sleep irregularities. For example, many adults suffer from sleep apnea, and many infants are lost because of sudden death infant syndrome (SIDS).

As technological advances are achieved, monitoring devices become smaller and less expensive. This allows advanced technologies to be placed in common households. Such devices can provide family members with warnings if the individual being monitored begins to exhibit symptoms that may require attention.

SUMMARY

Exemplary methods herein position a monitoring device adjacent a bed or crib (referred to generically herein as a "sleeping structure") position a camera of the monitoring device to detect movement and sounds of an individual (e.g., adult or infant human) lying within the sleeping structure, position a gas sensor of the monitoring device to detect gases surrounding the individual lying within the sleeping structure, and position a temperature and humidity sensor of the monitoring device to detect the temperature and humidity surrounding the individual lying within the sleeping structure. Such methods automatically monitor and evaluate the movement and sounds of the individual to identify individual movement and sound activities that are outside acceptable movement and sound tolerances, and monitor and evaluate the gases surrounding the individual and the temperature and humidity surrounding the individual to identify environmental conditions that are outside acceptable environmental tolerances (using a processor of the monitoring device that is operatively connected to the camera, gas sensor, and temperature and humidity sensor).

These methods automatically constantly and dynamically change the acceptable movement and sound tolerances and the acceptable environmental tolerances based on the age of the individual (input into a graphic user interface) and based on historical monitoring of the movement and sounds of the individual, historical monitoring of the gases surrounding the individual, and historical monitoring of the temperature and humidity surrounding the individual using the processor of the monitoring device. The acceptable movement and sound tolerances and/or the acceptable environmental tolerances can also be constantly and dynamically changed based on societal conditions in which the sleeping structure is located. Such societal conditions can include the family structure, family economic conditions, family health conditions, family dietary conditions, family drug use, family alcohol use, and family tobacco use of a family monitoring the individual within the sleeping structure.

Thus, the methods disclosed herein provide an audible warning and at least one electronic message warning when the monitored individual movement and sound activities are outside the acceptable movement and sound tolerances and/or the monitored environmental conditions are outside the acceptable environmental tolerances (using an input/output device of the monitoring device). For example, the percentage of carbon dioxide or the air temperature and humidity surrounding the individual may be too low or too high, or the movement and sounds detected by the camera can be consistent with an individual rolling over from sleeping on their back to sleeping face down on their front, etc., for the warnings to be triggered.

The electronic message warning comprises an electronic message (e.g., an electronic text message, an electronic social media webpage posting, a notification to an automated security system, etc.) transmitted over a computerized network operatively connected to the input/output device. The graphic user interface can similarly provide a graphic user interface warning (e.g., audible warning, light based warning, graphic based warning, etc.) based on the individual movement and sound activities being outside the acceptable movement and sound tolerances and/or the environmental conditions being outside the acceptable environmental tolerances.

Apparatus embodiments herein can include (among other components) a processor, a camera operatively connected to the processor, a gas sensor operatively connected to the processor, a temperature and humidity sensor operatively connected to the processor, an input/output device operatively connected to the processor, a graphic user interface operatively connected to the processor, etc. The camera is positioned to detect movement and sounds of an individual lying within a sleeping structure, the gas sensor is positioned to detect gases surrounding the individual lying within the sleeping structure, the temperature and humidity sensor is positioned to detect the temperature and humidity surrounding the individual lying within the sleeping structure, etc.

The processor monitors and evaluates the movement and sounds of the individual to identify individual movement and sound activities that are outside acceptable movement and sound tolerances. Similarly, the processor monitors and evaluates the gases surrounding the individual and the temperature and humidity surrounding the individual to identify environmental conditions that are outside acceptable environmental tolerances. The processor constantly and dynamically changes the acceptable movement and sound tolerances and the acceptable environmental tolerances based on the age of the individual and based on historical monitoring of the movement and sounds of the individual, historical monitoring of the gases surrounding the individual, and historical monitoring of the temperature and humidity surrounding the individual.

The processor can also constantly and dynamically change the acceptable movement and sound tolerances and the acceptable environmental tolerances based on societal conditions in which the sleeping structure is located. Such societal conditions include the family structure, family economic conditions, family health conditions, family dietary conditions, family drug use, family alcohol use, and family tobacco use of a family monitoring the individual within the sleeping structure.

The processor causes the input/output device to provide an audible warning and at least one electronic message warning based on the individual movement and sound activities being outside the acceptable movement and sound tolerances and/or the environmental conditions being outside the acceptable environmental tolerances. For example, the percentage of carbon dioxide or the air temperature and humidity surrounding the individual may be too low or too high, or the movement and sounds detected by the camera can be consistent with an individual rolling over from sleeping on their back to sleeping face down on their front, etc., for the warnings to be triggered.

Again, the electronic message warning comprises an electronic message (e.g., an electronic text message, an electronic social media webpage posting, a notification to an automated security system, etc.) transmitted over a computerized network operatively connected to the input/output device. The graphic user interface can similarly provide a graphic user interface warning (e.g., audible warning, light based warning, graphic based warning, etc.) based on the individual movement and sound activities being outside the acceptable movement and sound tolerances and/or the environmental conditions being outside the acceptable environmental tolerances.

These and other features are described in, or are apparent from, the following detailed description.

BRIEF DESCRIPTION OF THE DRAWINGS

Various exemplary systems and methods are described in detail below, with reference to the attached drawing figures, in which.

DETAILED DESCRIPTION

Systems and methods herein provide a monitoring device (e.g., a stand-alone device, mobile phone/tablet, network-connected Web cam, etc.) to monitor a sleeping individual (an infant or adult). Monitoring devices can be mounted in baby mobiles, ceiling fans, lamps, or other devices that are above or in close proximity to a sleeping infant or adult, providing a good viewing angle, convenience, but not requiring additional infrastructure (i.e., tripods or other complex mounts that take up space in the room). Power or charging capabilities can be built into the mounting devices.

The devices herein can use video and audible monitoring to detect conditions that can result in SIDS, for example. Additionally, with devices such as mobile phones, other monitoring can be employed through standard interfaces. Some monitoring techniques herein include video, audio, gas detection, temperature detection, etc.

With respect to video detection, the facial and movement recognition of modern video capture technology are used to recognize an infant's face, and other relevant focal points, such as the front of their pajamas. Then, the monitoring device can detect when the infant is potentially going to roll over into the prone (face down) position, as one of the proposed causes of SIDS is infants suffocating while lying in the prone position.

The methods and systems herein set and constantly and dynamically revise alarm thresholds, so that guardians are alerted when the infant looks like they might roll over, but before it has actually happened. Turning also enables the monitoring device to adapt as the infants develop new capabilities (i.e., as they grow and are more likely to roll over, or as gain strength and are less likely to suffocate). Video monitoring can also be used to determine whether an infant is breathing.

Video monitoring can also track movement in general, and record the number of minutes since a movement was last detected, in an attempt to determine whether there is a problem. Methods and systems herein have a learning mode to determine how often a given individual generally moves during sleep, and detect deviations from the normal pattern of the individual. Basic video monitoring is somewhat dependent on the amount of light in the room, and infrared and other night vision technologies are used in methods and systems herein.

With respect to audio detection, the monitoring devices herein include a microphone to monitor for breathing and other noises that can signal either safe or harmful conditions. These can include normal or abnormal breathing patterns, coughing, wheezing, choking, or stopped breathing. With methods and devices herein, an individuals "normal" pattern of movement and sounds can be learned over time, and deviations from the learned "normal" pattern is considered abnormal.

Additionally, the alarm notification thresholds are constantly and dynamically revised by devices and methods herein. Infants are at highest risk of SIDS from age 2-4 months, with risk decreasing before and after this age. During this time, or if a child has other SIDS attributes (low birth rate, not breastfeeding, parents smoking, etc.), the devices and methods herein automatically become more sensitive (i.e., alerting if a baby is even remotely showing signs of rolling over or other unsafe activities). As the child gets older and stronger (i.e., due to more tummy time), the devices and methods herein automatically become less sensitive.

Methods and systems herein can detect other specific conditions, such as an infant spitting up in a way that might cause them to choke (based, for example, on matches to learned movement patterns or sound patterns associated with such activity) or can detect the presence of blankets, toys, pillows or other potentially harmful objects being left in the crib, or in a position that endangers the infant (e.g., covering the individual's face) based on shape and position recognition capabilities. Additionally, shortcomings in imaging capabilities of current devices (i.e., smartphones) are overcome with methods and systems herein by connecting a more advanced imaging device (i.e., standalone video camera with night vision capabilities) via USB (universal serial bus connector), Wi-Fi (wireless fidelity protocol), bluetooth, or other standard connectors.

Thus, with methods and systems herein, measurement instruments can be connected to mobile phones, such as sensors that measure carbon dioxide, temperature, or humidity levels. Carbon dioxide poisoning is one proposed cause of SIDS, as it is believed SIDS may be caused by an infant's weak lungs not properly expelling carbon dioxide. Temperature and humidity can be measured to assure that the room stays temperate to support proper breathing, as high temperature and humidity are also suspected contributing factors for SIDS.

The methods and devices herein notify guardians and other family members in the event of a possible SIDS condition. Notifications here are triggered by the events/unsafe conditions discussed above. Alerts can be sent via all possible mechanisms instantly, or in a chain of escalations if no one responds (i.e., first audible alarms, then send text and email messages, then place phone calls). The possible forms of notification available in the monitoring devices include, but are not limited to, a speaker, calling, texting, email, posting on social networks, streaming, home automation system integration, etc. Thus, for example, the devices herein are equipped with a speaker to make noise, in an attempt to wake the infant and their guardians. The devices herein can place phone calls to guardians' mobile phones (since today many adults sleep with their phones close by on their nightstand), home phone, neighbors, family members, etc. The devices herein can call 911 or security services companies directly as a last resort. Additionally, the devices herein can send text messages to mobile phones of guardians, neighbors, family members, etc.; can send email messages to guardians, neighbors, family members, etc.; can post alerts to social networks and services; etc.

Similarly, the devices herein can stream the video and audio remotely, in the event that a distant relative is the only person that can be reached. For example, if the guardian in the same location as the infant does not respond to the notifications, the video and audio can be streamed to someone else (relative, neighbor, etc.) who can confirm the presence of a possible SIDS condition and call 911 if they are not able to awaken the guardian.

With respect to home automation system integration, the devices herein have Wi-Fi or other compatible technologies and can connect to home automation systems to turn on the lights, sound burglar alarms, enable heating ventilation and air-conditioning (HVAC) systems (furnace, A/C, etc.; again improper room temperature is believed to contribute to SIDS and some studies have found that moving air reduces SIDS occurrences), turn on a furnace blower fan, ceiling fan or box fan (by enabling or disabling outlets for example or by controlling the devices directly), turn on home theater systems to play music, trigger smoke sensor alarms, or perform other actions that resolve the SIDS conditions or awaken the guardians.

A mobile phone or Webcam can be used to implement the methods described herein (with or without additional instrumentation attached). Such mobile devices are a useful option, since modern devices already include many available connectivity options (cellular, Wi-Fi, Bluetooth). All of the alerting and notification options are available over the Internet without cellular connectivity (i.e., placing phone or video calls via voice over Internet protocol (VOIP), sending text messages via free Internet-based text messaging Web sites, etc.).

Figure 1:
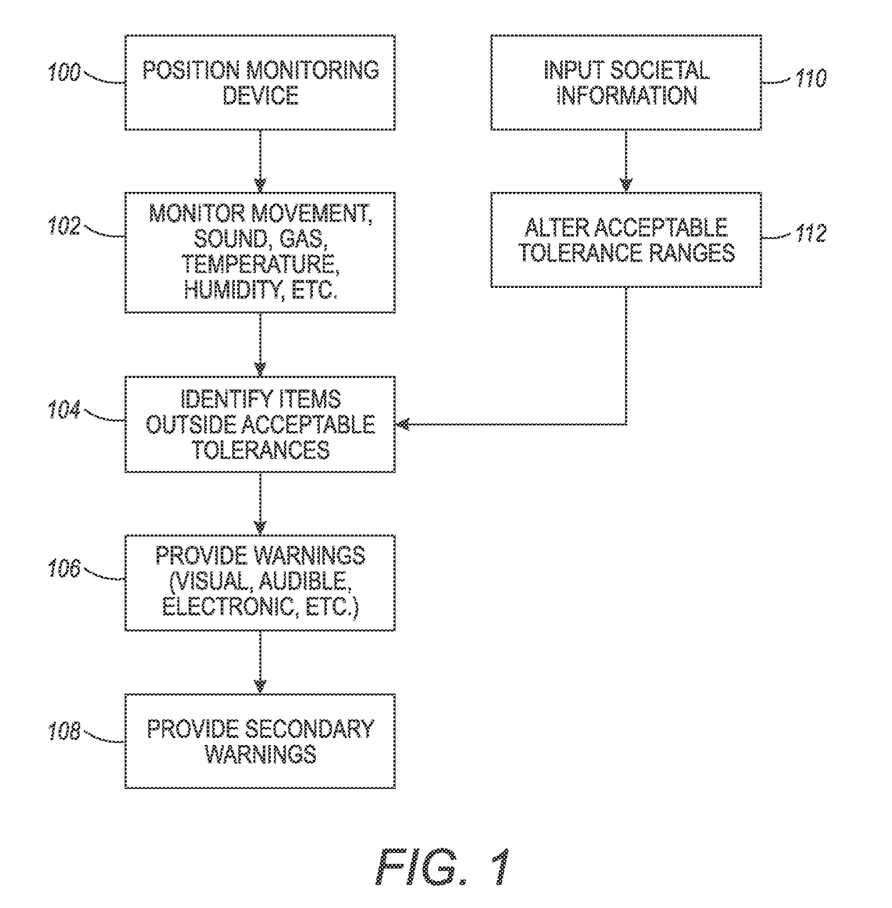
FIG. 1 is a flow diagram of various methods herein.

FIG. 1 is flowchart illustrating exemplary methods herein. In item 100, these methods position a monitoring device adjacent a bed or crib (referred to generically herein as a "sleeping structure"). Because the monitoring device includes or is connected to a camera and various sensors (gas, temperature, humidity, etc.) item 100 includes positioning a camera of the monitoring device to detect movement and sounds of an individual (e.g., adult or infant human) lying within the sleeping structure, positioning a gas sensor of the monitoring device to detect gases surrounding the individual lying within the sleeping structure, and positioning a temperature and humidity sensor of the monitoring device to detect the temperature and humidity surrounding the individual lying within the sleeping structure.

In item 102, such methods automatically monitor the movement and sounds of the individual, the gases surrounding the individual, the temperature and humidity surrounding the individual. The aspects that are monitored in item 102 are only limited by the sensors that are within or connected to the monitoring device.

Such methods evaluate the movement and sounds of the individual to identify individual movement and sound activities that are outside acceptable movement and sound tolerances, and monitor and evaluate the gases surrounding the individual and the temperature and humidity surrounding the individual to identify environmental conditions that are outside acceptable environmental tolerances (using a processor of the monitoring device that is operatively connected to the camera, gas sensor, and temperature and humidity sensor). Thus, as shown in item 104, these methods identify items (movement, sounds, gases, temperature, humidity, etc.) that are outside acceptable tolerance ranges.

Societal information is input by the user or operator in item 110. Such societal conditions can include the age, weight, gender, race, health, etc., of the individual being monitored, as well as the family structure, family economic conditions, family health conditions, family dietary conditions, family drug use, family alcohol use, and family tobacco use of the family monitoring the individual within the sleeping structure.

In item 112, these methods automatically constantly and dynamically change the acceptable movement and sound tolerances based on historical monitoring of the movement and sounds of the individual and the acceptable environmental tolerances based on the societal information of the individual input in item 110 (input into a graphic user interface) and the historical monitoring of the gases surrounding the individual, historical monitoring of the temperature and humidity surrounding the individual using the processor of the monitoring device. The acceptable movement and sound tolerances and/or the acceptable environmental tolerances constantly and dynamically change as the societal conditions change (the individual ages, become larger, becomes less ill, or more or less smokers move in our out of the house) in addition to as the individuals breathing habits, movement habits, temperature, etc., change.

For example, an individual with sleep apnea using the devices disclosed herein can enter (into the graphic user interface) various medical information (age, weight, seriousness of sleep apnea, whether they use treatment devices while sleeping, etc.) as well as societal information. With this input, the methods and devices herein can establish baseline acceptable movement and sound tolerances and baseline acceptable environmental tolerances. The methods and devices herein then automatically keep track of the monitored individual's age as time progresses, and record the monitored individual's movement, sounds made, carbon dioxide emitted, sleeping temperature and humidity, etc., during sleeping over an extended period of time (e.g., multiple nights, multiple weeks, multiple months, multiple years, etc.). As time progresses, the methods and systems herein adjust all tolerance ranges, such as the movement and sound tolerances, and the environmental tolerances from the baseline level to a different level based on the age, movement, sounds made, carbon dioxide emitted, sleeping temperature and humidity, etc., of the monitored individual tracked over time.

For example, if the individual is a very active sleeper and has a higher movement level during sleeping relative to the baseline acceptable movement level, the acceptable movement level will be elevated so that false alarms are not generated for excessive movement. Conversely, if an individual has unusually low activity during sleeping, the acceptable movement level can be decreased so that false alarms are not generated for very low movement levels. In a similar way, the acceptable tolerance levels for each item measured is individually adjusted based upon observations gained over time by the various sensors of the devices described herein.

In another example, if the devices described herein are set up for a newborn infant, as the infant ages, the movement sensitivity threshold can be decreased during the period of highest risk for SIDS (2-4 months) and then decreased thereafter. In addition, as societal conditions change (a smoker moves into the household) the user can update this information through the graphic user interface and different tolerances can be changed based upon how this would increase or decrease SIDS related parameters.

Further, the methods and devices herein match the pattern of current activities of the sleeping individual with preprogrammed activities known to be related to high risk situations. For example, if a carbon dioxide level below an acceptable threshold is present, if a temperature level or humidity level above an acceptable threshold is present, if excessive movement levels above an acceptable movement threshold are present, etc., an alarm will be triggered. In addition, combinations of different levels exceeding a threshold may be required before alarms are triggered. Therefore, if the movement level is below the acceptable threshold, but the carbon dioxide level is within acceptable thresholds (indicating that proper breathing is occurring) an alarm may not be generated.

Therefore, the methods and devices described herein utilize user input, historical tracking of "normal" conditions of the specific individual being monitored, measured physical characteristics from sensor input, and processes that identify patterns indicating high risk situations, to constantly change tolerance levels so that false alarms are not generated.

In item 106, when the monitored individual movement and sound activities are outside the acceptable movement and sound tolerances and/or the monitored environmental conditions are outside the acceptable environmental tolerances, the methods disclosed herein provide an audible warning and at least one electronic message warning (using an input/output device of the monitoring device). For example, the percentage of carbon dioxide or the air temperature and humidity surrounding the individual may be too low or too high, or the movement and sounds detected by the camera can be consistent with an individual rolling over from sleeping on their back to sleeping face down on their front, etc., for the warnings to be triggered in item 106.

The electronic message warning provided in item 106 comprises an electronic message (e.g., an electronic text message, an electronic social media webpage posting, a notification to an automated security system, etc.) transmitted over a computerized network operatively connected to the input/output device. The graphic user interface can similarly provide a graphic user interface warning (e.g., audible warning, light based warning, graphic based warning, etc.) based on the individual movement and sound activities being outside the acceptable movement and sound tolerances and/or the environmental conditions being outside the acceptable environmental tolerances. In item 108, the methods disclosed herein can provide secondary warnings in a chain of escalating warnings (i.e., first audible alarms, then send text and email messages, then place phone calls, etc.).

Figure 2:
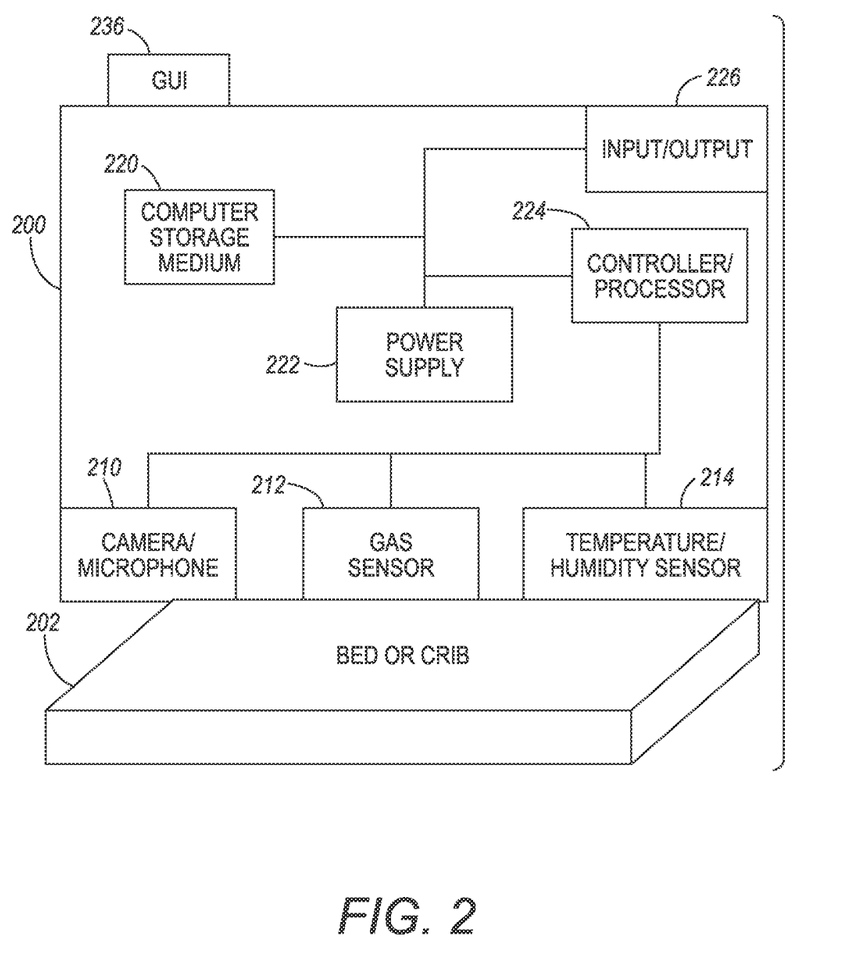
FIG. 2 is a schematic diagram illustrating devices herein.

FIG. 2 illustrates a computerized device 200, which can be used with systems and methods herein and can comprise, for example, stand-alone device, mobile phone/tablet, network-connected Web cam, etc., a personal computer, a portable computing device, etc. The computerized device 200 includes a controller/processor 224 and a communications port (input/output) 226 operatively connected to the processor 224 and to the computerized network 232 external to the computerized device 200. Also, the computerized device 200 can include at least one accessory functional component, such as a graphic user interface assembly 236, a camera/microphone 210, a gas sensor 212, a temperature/humidity sensor 214, etc. While a limited number of sensors are mentioned in the examples herein, those ordinarily skilled in the art would understand that the methods and devices herein could utilize many more sensors, depending upon the specific medical condition being monitored, the cost of the sensors, the reliability of sensors, ease of the sensors to communicate with other devices, etc. Therefore, the devices and methods herein are not limited to the exemplary sensors discussed here.

Figure 3:
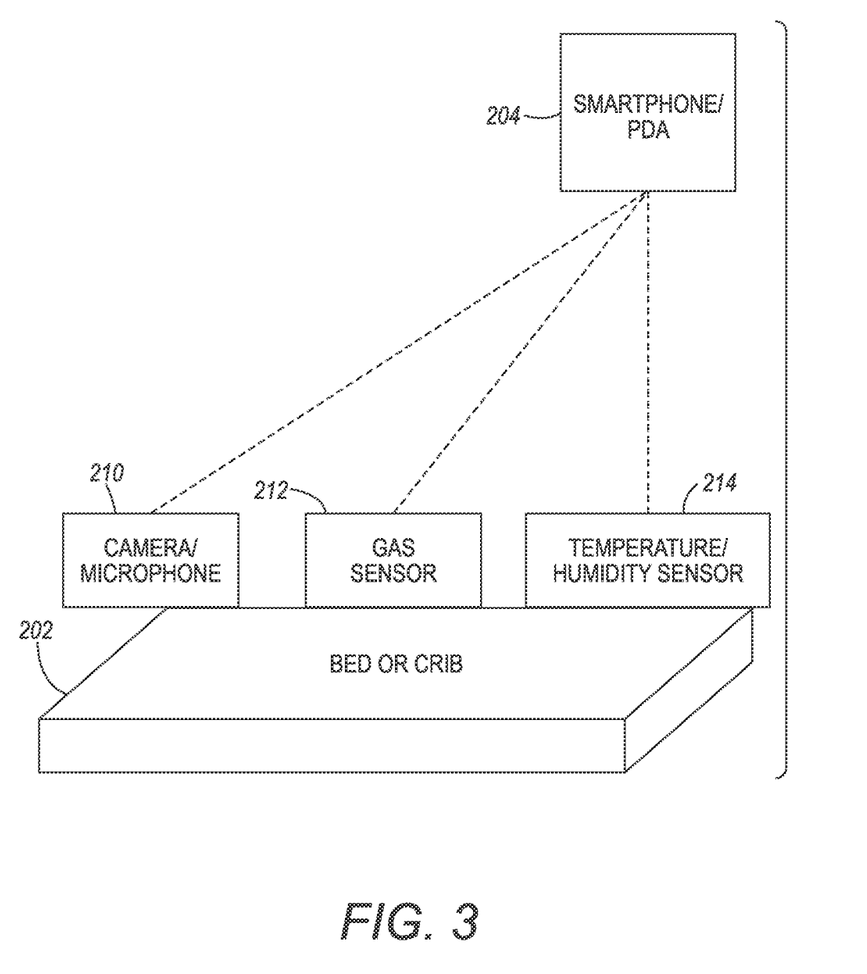
FIG. 3 is a schematic diagram illustrating devices herein.

In an alternative embodiment shown in FIG. 3, a separate computerized device 204 (which in this example is a smart phone or other form of personal digital assistant (PDA), such as a tablet, etc.) is wirelessly connected to (or wired to) the camera/microphone 210, gas sensor 212, temperature/humidity sensor 214, etc. (which can be individual devices or combined into a single device). In one example, the camera/microphone 210, gas sensor 212, temperature/humidity sensor 214, etc. are included in the frame of the crib or bed 202, and wirelessly communicate with the separate computerized device 204, which can be running a computer program (or app) performing the methods described herein. The computerized device 204 can include many of the components discussed in device 200, but such are not illustrated to avoid clutter in the drawings.

The input/output device 226 is used for communications (wired or wireless) to and from the computerized device 200. The processor 224 controls the various actions of the computerized device 200/204. A non-transitory computer storage medium device 220 (which can be optical, magnetic, capacitor based, etc.) is readable by the processor 224 and stores instructions that the processor 224 executes to allow the computerized device 200/204 to perform its various functions, such as those described herein. Thus, as shown in FIGS. 2 and 3, a body housing 200/204 has one or more functional components that operate on power supplied by the power supply 222. The power supply 222 can comprise a power storage element (e.g., a battery) and/or can be connected to an external alternating current power source and can convert the external power into the type of power needed by the various components.

The camera/microphone 210 is positioned adjacent the sleeping structure (or is an integral part of the sleeping structure) to detect movement and sounds of an individual lying within a sleeping structure, the gas sensor 212 is similarly positioned adjacent the sleeping structure (or is an integral part of the sleeping structure) to detect gases surrounding the individual lying within the sleeping structure, the temperature and humidity sensor 214 is again positioned adjacent the sleeping structure (or is an integral part of the sleeping structure) to detect the temperature and humidity surrounding the individual lying within the sleeping structure, etc.

The processor 224 monitors and evaluates the movement and sounds of the individual to identify individual movement and sound activities that are outside acceptable movement and sound tolerances. Similarly, the processor 224 monitors and evaluates the gases surrounding the individual and the temperature and humidity surrounding the individual to identify environmental conditions that are outside acceptable environmental tolerances. The processor 224 constantly and dynamically changes the acceptable movement and sound tolerances and the acceptable environmental tolerances based on the age of the individual and based on historical monitoring of the movement and sounds of the individual, historical monitoring of the gases surrounding the individual, and historical monitoring of the temperature and humidity surrounding the individual.

The processor 224 can also constantly and dynamically change the acceptable movement and sound tolerances and the acceptable environmental tolerances based on societal conditions in which the sleeping structure is located. Such societal conditions include the family structure, family economic conditions, family health conditions, family dietary conditions, family drug use, family alcohol use, and family tobacco use of a family monitoring the individual within the sleeping structure.

The processor 224 causes the input/output device to provide an audible warning and at least one electronic message warning based on the individual movement and sound activities being outside the acceptable movement and sound tolerances and/or the environmental conditions being outside the acceptable environmental tolerances.

Figure 4:
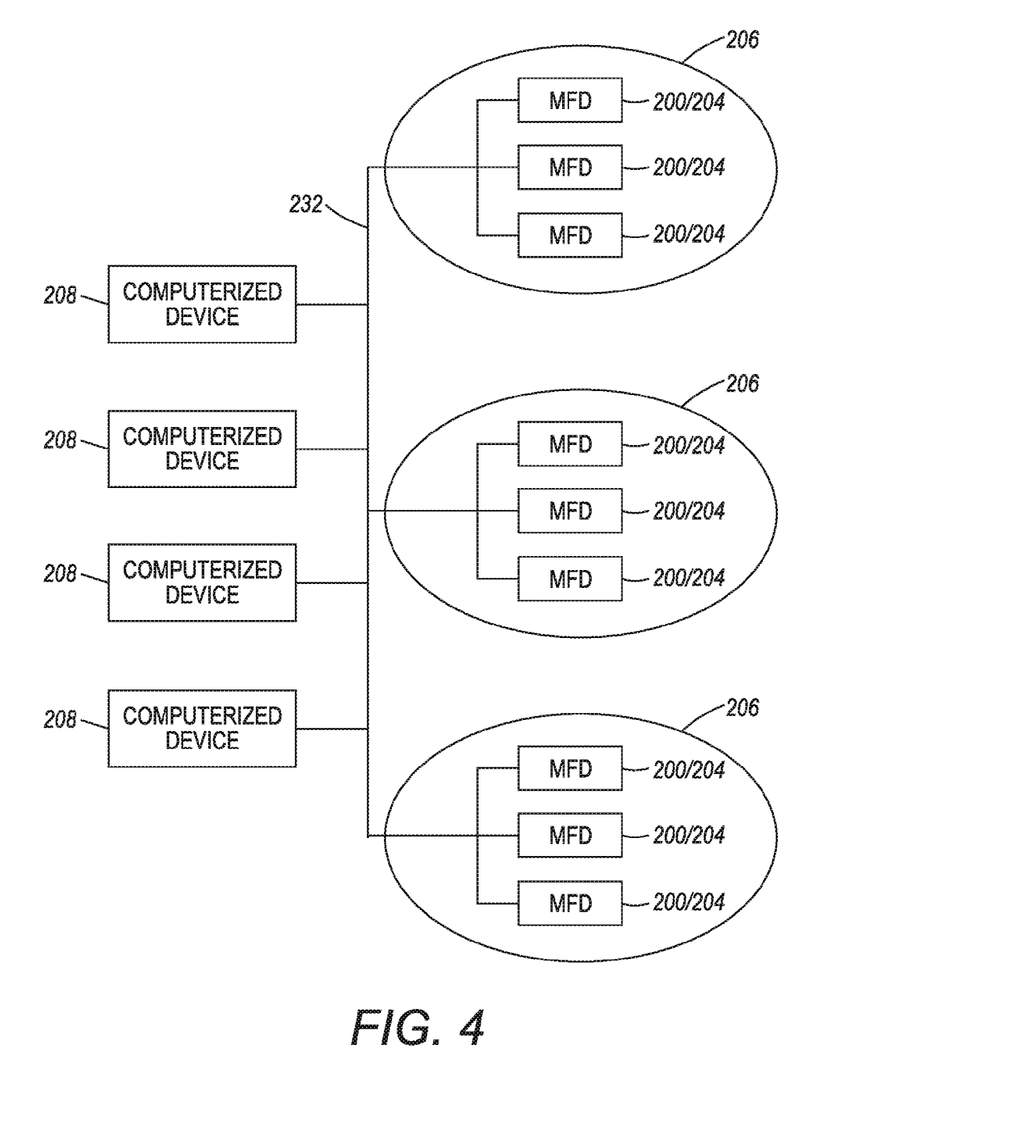
FIG. 4 is a schematic diagram illustrating systems herein.

As shown in FIG. 4, exemplary system systems and methods herein include various computerized monitoring devices 200, 204 located at various different physical locations 206. Other computerized devices, that can include alarm devices, text message servers, social media servers, lighting systems, phone system servers, personal computers, etc., and are in communication with (operatively connected to) the computerized monitoring devices 200, 204 by way of a local or wide area (wired or wireless) network 202.

The warnings are provided when the individual movement and sound activities are outside the acceptable movement and sound tolerances and/or the environmental conditions are outside the acceptable environmental tolerances comprise audible and visual warnings, as well as electronic warnings. Such electronic warnings can include, for example, an electronic message (e.g., an electronic text message, an electronic social media webpage posting, a notification to an automated security system, etc.) transmitted over the computerized network 202/208 operatively connected to the input/output device 226. The graphic user interface 236 can similarly provide a graphic user interface warning (e.g., audible warning, light based warning, graphic based warning, etc.) based on the individual movement and sound activities being outside the acceptable movement and sound tolerances and/or the environmental conditions being outside the acceptable environmental tolerances.

In addition, terms such as "right", "left", "vertical", "horizontal", "top", "bottom", "upper", "lower", "under", "below", "underlying", "over", "overlying", "parallel", "perpendicular", etc., used herein are understood to be relative locations as they are oriented and illustrated in the drawings (unless otherwise indicated). Terms such as "touching", "on", "in direct contact", "abutting", "directly adjacent to", etc., mean that at least one element physically contacts another element (without other elements separating the described elements). Further, the terms automated or automatically mean that once a process is started (by a machine or a user), one or more machines perform the process without further input from any user.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. Unless specifically defined in a specific claim itself, steps or components of the systems and methods herein cannot be implied or imported from any above example as limitations to any particular order, number, position, size, shape, angle, color, or material.

What is claimed is:

1. An apparatus comprising:
a processor;
a camera operatively connected to said processor;
an input/output device operatively connected to said processor; and
a graphic user interface operatively connected to said processor, an age of an individual within a sleeping structure being input into said graphic user interface,
said camera being positioned to detect movement and sounds of said individual,
said processor keeping track of a monitored age as time progresses based on said age input into said graphic user interface,
said processor evaluating said movement and sounds of said individual to identify individual movement and sound activities that are outside acceptable movement and sound tolerances,
said processor constantly and dynamically changing said acceptable movement and sound tolerances based on said monitored age of said individual and based on historical monitoring of said movement and sounds of said individual,
said processor causing said input/output device to provide an audible warning and at least one electronic message warning based said individual movement and sound activities being outside said acceptable movement and sound tolerances, and
said electronic message warning comprising an electronic message transmitted over a computerized network operatively connected to said input/output device.

2. The apparatus according to claim 1, said graphic user interface providing a graphic user interface warning based on said individual movement and sound activities being outside said acceptable movement and sound tolerances.

3. The apparatus according to claim 1, said electronic message warning comprising at least one of: an electronic text message, an electronic social media webpage posting, and a notification to an automated security system.

4. The apparatus according to claim 1, said processor constantly and dynamically changing said acceptable movement and sound tolerances based on societal conditions in which said sleeping structure is located.

5. The apparatus according to claim 4, said societal conditions comprising family structure, family economic conditions, family health conditions, family dietary conditions, family drug use, family alcohol use, and family tobacco use of a family monitoring said individual within said sleeping structure.

6. The apparatus according to claim 1, said movement and sounds of said individual comprising movement and sounds consistent with said individual rolling over from an individual back to an individual front.

7. An apparatus comprising:
a processor;
a camera operatively connected to said processor;
a gas sensor operatively connected to said processor;
a temperature and humidity sensor operatively connected to said processor; and
an input/output device operatively connected to said processor; and
a graphic user interface operatively connected to said processor, an age of an individual within a sleeping structure being input into said graphic user interface,
said camera being positioned to detect movement and sounds of said individual,
said gas sensor being positioned to detect gases surrounding said individual within said sleeping structure,
said temperature and humidity sensor being positioned to detect a temperature and humidity surrounding said individual within said sleeping structure,
said processor keeping track of a monitored age as time progresses based on said age input into said graphic user interface,
said processor evaluating said movement and sounds of said individual to identify individual movement and sound activities that are outside acceptable movement and sound tolerances,
said processor evaluating said gases surrounding said individual and said temperature and humidity surrounding said individual to identify environmental conditions that are outside acceptable environmental tolerances, said processor constantly and dynamically changing said acceptable movement and sound tolerances and said acceptable environmental tolerances based on said monitored age of said individual and based on historical monitoring of said movement and sounds of said individual, historical monitoring of said gases surrounding said individual, and historical monitoring of said temperature and humidity surrounding said individual, said processor causing said input/output device to provide an audible warning and at least one electronic message warning based on at least one of said individual movement and sound activities being outside said acceptable movement and sound tolerances and said environmental conditions being outside said acceptable environmental tolerances, and said electronic message warning comprising an electronic message transmitted over a computerized network operatively connected to said input/output device.

8. The apparatus according to claim 7, said graphic user interface providing a graphic user interface warning based on at least one of said individual movement and sound activities being outside said acceptable movement and sound tolerances and said environmental conditions being outside said acceptable environmental tolerances.

9. The apparatus according to claim 7, said electronic message warning comprising at least one of: an electronic text message, an electronic social media webpage posting, and a notification to an automated security system.

10. The apparatus according to claim 7, said processor constantly and dynamically changing said acceptable movement and sound tolerances and said acceptable environmental tolerances based on societal conditions in which said sleeping structure is located.

11. The apparatus according to claim 10, said societal conditions comprising family structure, family economic conditions, family health conditions, family dietary conditions, family drug use, family alcohol use, and family tobacco use of a family monitoring said individual within said sleeping structure.

12. The apparatus according to claim 7, said gases surrounding said individual comprising a percentage of carbon dioxide surrounding said individual, and said movement and sounds of said individual comprising movement and sounds consistent with said individual rolling over from an individual back to an individual front.

13. A method comprising:

positioning a monitoring device adjacent a sleeping structure;

positioning a camera of said monitoring device to detect movement and sounds of an individual within said sleeping structure;

receiving an age of said individual into a graphic user interface;

keeping track of a monitored age as time progresses based on said age input into said graphic user interface;

automatically evaluating said movement and sounds of said individual to identify individual movement and sound activities that are outside acceptable movement and sound tolerances using a processor of said monitoring device, said processor being operatively connected to said camera;

automatically constantly and dynamically changing said acceptable movement and sound tolerances based on said monitored age of said individual and based on historical monitoring of said movement and sounds of said individual using said processor of said monitoring device; and providing an audible warning and at least one electronic message warning based on said individual movement and sound activities being outside said acceptable movement and sound tolerances using an input/output device of said monitoring device, said processor being operatively connected to said input/output device, and said electronic message warning comprising an electronic message transmitted over a computerized network operatively connected to said input/output device.

14. The method according to claim 13, said graphic user interface providing a graphic user interface warning based on said individual movement and sound activities being outside said acceptable movement and sound tolerances.

15. The method according to claim 13, said providing said electronic message warning comprising providing at least one of: an electronic text message, an electronic social media webpage posting, and a notification to an automated security system.

16. The method according to claim 13, said constantly and dynamically changing said acceptable movement and sound tolerances being based on societal conditions in which said sleeping structure is located.

17. The method according to claim 16, said societal conditions comprising family structure, family economic conditions, family health conditions, family dietary conditions, family drug use, family alcohol use, and family tobacco use of a family monitoring said individual within said sleeping structure.

18. The method according to claim 13, said movement and sounds of said individual comprising movement and sounds consistent with said individual rolling over from an individual back to an individual front.

19. A method comprising:

positioning a monitoring device adjacent a sleeping structure;

positioning a camera of said monitoring device to detect movement and sounds of an individual within said sleeping structure;

positioning a gas sensor of said monitoring device to detect gases surrounding said individual within said sleeping structure;

positioning a temperature and humidity sensor of said monitoring device to detect a temperature and humidity surrounding said individual within said sleeping structure;

receiving an age of said individual into a graphic user interface;

keeping track of a monitored age as time progresses based on said age input into said graphic user interface;

automatically evaluating said movement and sounds of said individual to identify individual movement and sound activities that are outside acceptable movement and sound tolerances, using a processor of said monitoring device, said processor being operatively connected to said camera, said gas sensor, and said temperature and humidity sensor;

automatically evaluating said gases surrounding said individual and said temperature and humidity surrounding said individual to identify environmental conditions that are outside acceptable environmental tolerances using said processor;

automatically constantly and dynamically changing said acceptable movement and sound tolerances and said acceptable environmental tolerances based on said monitored age of said individual and based on historical monitoring of said movement and sounds of said individual, historical monitoring of said gases surrounding said individual, and historical monitoring of said temperature and humidity surrounding said individual using said processor of said monitoring device; and providing an audible warning and at least one electronic message warning based on at least one of said individual movement and sound activities being outside said acceptable movement and sound tolerances and said environmental conditions being outside said acceptable environmental tolerances using an input/output device of said monitoring device, said electronic message warning comprising an electronic message transmitted over a computerized network operatively connected to said input/output device.

20. The method according to claim 19, said graphic user interface providing a graphic user interface warning based on at least one of said individual movement and sound activities being outside said acceptable movement and sound tolerances and said environmental conditions being outside said acceptable environmental tolerances.

21. The method according to claim 19, said providing said electronic message warning comprising providing at least one of: an electronic text message, an electronic social media webpage posting, and a notification to an automated security system.

22. The method according to claim 19, said constantly and dynamically changing said acceptable movement and sound tolerances and said acceptable environmental tolerances being based on societal conditions in which said sleeping structure is located.

23. The method according to claim 22, said societal conditions comprising family structure, family economic conditions, family health conditions, family dietary conditions, family drug use, family alcohol use, and family tobacco use of a family monitoring said individual within said sleeping structure.

24. The method according to claim 19, said gases surrounding said individual comprising a percentage of carbon dioxide surrounding said individual, and said movement and sounds of said individual comprising movement and sounds consistent with said individual rolling over from an individual back to an individual front.

* * * * *